United States Patent [19]

Chiang

[11] 4,195,038

[45] Mar. 25, 1980

[54] PREPARATION OF 3-BROMO-2-HYDROXY-4,4,5,5-TETRAMETHYLCYCLOPENTA-2-ENONE

[75] Inventor: Yunn H. Chiang, Andover, Mass.

[73] Assignee: Polaroid Corporation, Cambridge, Mass.

[21] Appl. No.: 938,939

[22] Filed: Sep. 1, 1978

Related U.S. Application Data

[63] Continuation-in-part of Ser. No. 796,011, May 11, 1977, abandoned.

[51] Int. Cl.² ............................................. C07C 45/00
[52] U.S. Cl. ............................ 260/586 C; 260/586 R; 260/593 H
[58] Field of Search ............ 260/586 C, 593 H, 586 R

[56] References Cited

U.S. PATENT DOCUMENTS

| 3,180,893 | 4/1965 | Robinson et al. | 260/586 C |
| 3,615,440 | 10/1971 | Bloom et al. | 96/29 R |

OTHER PUBLICATIONS

Francis et al., "J. Chem. Soc.", vol. 1913, 2238 (1913).
Hesse et al., "Ann.", vol. 679, p. 100 (1964).
Claisen, "Ann. der Chemie", vol. 180, pp. 10–14 (1875).
Shoppee et al., "J. Chem. Soc. (c)", 1969, 1346–1349 (1969).
Francis et al., "J. Chem. Soc.", 1913, 2238.
Ingold et al., "J. Chem. Soc.", 1928, 365.

*Primary Examiner*—Norman Morgenstern
*Attorney, Agent, or Firm*—Gaetano D. Maccarone; Esther A. H. Hopkins

[57] ABSTRACT

Bromination of large batches of 2,6-dimethyl-2,5-heptadiene-4-one below −20° C. followed by dehydrobromination without intermediate isolation and recrystallization to produce 3,5-dibromo-2,6-dimethyl-2,5-heptadiene-4-one which can be cyclized without isolation to high yields of 3-bromo-2-hydroxy-4,4,5,5-tetramethylcyclopenta-2-enone is disclosed.

9 Claims, No Drawings

PREPARATION OF 3-BROMO-2-HYDROXY-4,4,5,5-TETRAMETHYL-CYCLOPENTA-2-ENONE

This is a continuation-in-part of application Ser. No. 796,011 filed May 11, 1977 in the name of Yunn H. Chiang and now abandoned.

This invention relates to chemistry. More precisely, the invention disclosed herein relates to an improved process for producing compounds useful as intermediates in the synthesis of tetramethylreductic acid.

Use of tetramethylreductic acid as a silver halide developing agent is described in U.S. Pat. No. 3,615,440 issued Oct. 26, 1971 to Stanley M. Bloom and Richard D. Cramer. This compound has been prepared according to the procedures disclosed by Francis and Willson, *Journal of the Chemical Society*, page 2238 (1913) and Hesse and Wehling, *Annalen* 679, page 100 (1964). Thus, for example, it has been recognized that one can readily produce tetramethylreductic acid by reacting phorone with bromine to give a tetrabromide, which eliminates hydrogen bromide by treatment with pyridine. The resulting dibromophorone is cyclized with loss of hydrogen bromide by sulfuric acid, and a bromine atom on the cyclized material is displaced with hydroxide to give tetramethylreductic acid. The bromination of phorone, 2,6-dimethyl-2,5-heptadiene-4-one, is carried out on a bench scale by addition of a solution of bromine in carbon tetrachloride to a carbon tetrachloride solution of phorone at 10°–15° C. The oily material obtained after removal of solvent must be crystallized from methanol to give high purity tetrabromophorone (2,3,5,6-tetrabromo-2,6-dimethyl-4-heptanone):

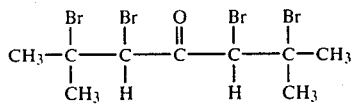

which can be dehydrobrominated to dibromophorone, (3,5-dibromo-2,6-dimethyl-2,5-heptadiene-4-one):

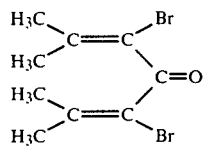

Quantitative yields of dibromophorone can be obtained from high-purity tetrabromophorone, but not from low purity material that is, unrecrystallized or oily material. Purification of tetrabromophorone in large quantity requires extended exposure of the material to methanol at elevated temperatures which leads to solvolysis and the decreased yields that accompany it. Preparation of dibromophorone from phorone, therefore, requires either recrystallization from hot alcohol of the intermediate tetrabromohprone formed in the usual bromination reaction or the preparation of pure intermediate.

Claisen, *Annalen der Chemie*, 180 p. 10–14 (1875) described the preparation of the tetrabromophorone and its recrystallization from hot alcohol. Francis and Willson, supra, prepared tetrabromophorone by the method of Claisen and described the laboratory scale preparation of dibromophorone in quantitative yield from tetrabromophorone by dehydrobromination in cold pyridine.

It has been found that scale-up of this process, i.e., bromination of phorone, recrystallization of the tetrabromophorone followed by dehydrobromination to dibromophorone, from bench to production scale leads to an increase in the extent of the solvolysis reaction resulting in poor yields.

Tetrabromophorone prepared by the above-designated method is contaminated by an impurity resulting from a partial allylic bromination, i.e., substitution on one of the methyl groups of phorone, which occurs as a side reaction when bromine is added. It would be advantageous to prepare tetrabromophorone sufficiently pure to be used directly in the dehydrobromination reaction without further purification. This would permit bypassing the solvent crystallization and the concomitant solvolysis problem. The dibromophorone thus prepared may be cyclized to bromoreductic acid.

It is therefore a primary object of the invention to provide an improved process for the preparation of large quantities of dibromophorone which can be cyclized directly to large quantities of bromoreductic acid.

It is a further object of this invention to provide a process for preparing dibromophorone from phorone without an intermediate isolation and purification of the tetrabromophorone formed by the bromination of said phorone.

Other objects of the invention will in part be obvious and will in part appear hereinafter.

The invention accordingly comprises the process involving the several steps and the relation and order of one or more of such steps with respect to each of the others which are exemplified in the following detailed disclosure.

According to the present invention, it has been discovered that high yields of 3-bromo-2-hydroxy-4,4,5,5-tetramethylcyclopenta-2-enone (bromoreductic acid) can be produced from 2,6-dimethyl-2,5-heptadiene-4-one in large batches without isolation and purification of the intermediately formed compounds if certain conditions are established. First, bromination of large batches of 2,6-dimethyl-2,5-heptadiene-4-one, e.g., at least about 25 moles, and preferably about 125 moles, must yield a 2,3,5,6-tetrabromo-2,6-dimethyl-4-heptanone which is sufficiently pure so that the reaction mixture can be used directly for dehydrobromination without recrystallization to avoid extended exposure to hot alcohol. Recrystallization from hot alcohol provides pure 2,3,5,6-tetrabromo-1,6-dimethyl-4-heptanone but the exposure to the hot alcohol reduces the yield. The larger the batch prepared the longer the exposure to hot alcohol in the recrystallization procedure and therefore the lower the yield of pure material. The second condition requires the use of an appropriate dehydrobromination reagent. Third, a very strong protic acid must be used for the cyclization.

The reaction steps of the present invention follow:

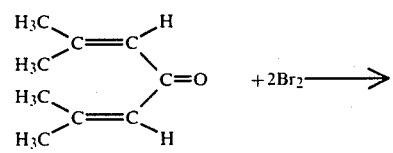

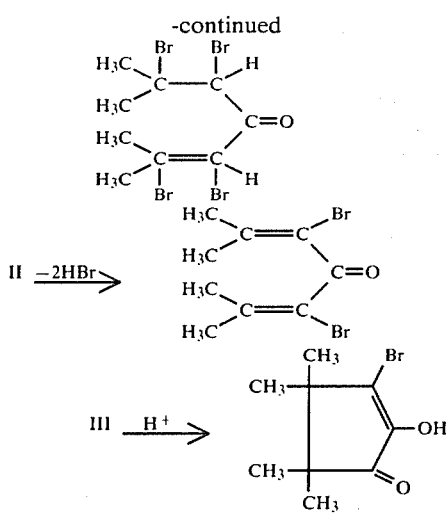

I is 2,6-dimethyl-2,5-heptadiene-4-one (phorone); II is 2,3,5,6-tetrabromo-2,6-dimethyl-4-heptanone (tetrabromophorone), III is 3,5-dibromo-2,6-dimethyl-2,5-heptadiene-4-one (dibromophorone), and IV is 3-bromo-2-hydroxy-4,4,5,5-tetramethyl-cyclopenta-2-enone (bromoreductic acid).

The present invention provides a process for preparing tetrabromophorone that does not generate the unwanted side products whose presence requires the undesirable purification step of the prior art. It was found that formation of the by-products due to substitution, rather than addition, could be suppressed by adding bromine to a solution of phorone maintained below about −20° C. and preferably below about −50° C. A convenient way to maintain such a low temperature is by addition of dry ice to the solvent. For this reason the bromination is preferably run at the temperature of a dry ice-solvent mixture.

The use of solvents such as carbon tetrachloride, chloroform and methylene chloride, for example, has led to good yields of the desired tetrabromophorone. Because it has a melting point and a boiling point lower than that of either carbon tetrachloride or chloroform, methylene chloride is the preferred solvent. For bromination reactions in this preferred solvent the temperature is that of a methylene chloride-dry ice bath, that is, about −70° C. Carbon tetrachloride, because of its high toxicity is not a preferred solvent although the bromination reaction in it leads to the desired addition product. The use of solvents such as glacial acetic acid, t-butanol and a 5:1 mixture of t-butanol and water provide product but in low yield.

It is not desirable to have unreacted bromine contaminating the tetrabromophorone because its presence would lead to substitution reactions, nor is it desirable to have unreacted phorone remaining at the end of the bromination, therefore the amount of bromine added is calculated to provide sufficient bromine to add to the two double bonds of phorone with no excess; that is, two molecular equivalents of bromine must be added for each molecular equivalent of phorone.

According to Henrikson, Cram and Hammond, Third Edition, McGraw-Hill Book Company, "[s]ynthetically, dehydrohalogenation (halide elimination) is carried out with strong bases which are not very nucleophilic at carbon such as $NH_2^-$, $R_2N^-$, $t\text{-}BuO^-$ or often $OH^-$ in order to suppress substitution." In the dehydrobromination reaction of the present invention the performance of various bases depends upon the concentration of the solution. The weaker the base, the higher the concentration of the tetrabromophorone needed for completing the reaction. For example, the addition of a stoichiometric amount of a strong base such as 1,4-diazabicyclo[2,2,2]octane to the reaction mixture wherein the tetrabromophorone has been formed results in yields of 75 to 80 percent of dibromophorone. On the other hand, quantitative conversion using pyridine as the dehydrobromination reagent requires a volume of pyridine at least equal to the volume of the solution of tetrabromophorone. To avoid the use of inordinately large quantities of pyridine, the solution of tetrabromophorone is reduced in volume before the addition of the dehydrobromination reagent, preferably by evaporation under vacuum.

Quantitative dehydrohalogenations can also be obtained with the use of morpholine as the dehydrobrominating reagent. Another dehydrobrominating reagent found useful was piperidine. Attempted dehydrobrominations with triethylamine did not yield dibromophorone but an unexpected cyclic product which, on the basis of infrared, proton and $C^{13}$ nuclear magnetic resonance and mass spectra, is believed to be:

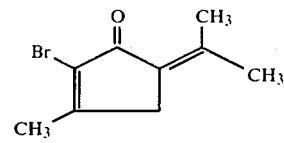

The dibromophorone may be cyclized using very strong protic acids such as trifluoroacetic acid, polyphosphoric acid or concentrated sulfuric acid. It was found that various Lewis acids as, for example, phosphorous oxychloride, anhydrous stannic chloride or a boron-trifluoride-methanol solution, produced no reaction and that the following acid media also failed to induce cyclization: formic acid, picric acid in chloroform, p-toluene-sulfonic acid in acetic acid or in dimethyl sulfoxide, trichloroacetic acid, trifluoroacetic acid in chloroform and 85% phosphoric acid.

The following examples are given to further illustrate the present invention and are not intended to limit the scope thereof.

EXAMPLE 1

Preparation of 2,3,5,6-tetrabromo-2,6-dimethyl-4-heptanone.

To a solution of 69.0 g (0.5 mole) of 99.8% pure 2,6-dimethyl-2,5-heptadiene-4-one in 800 ml of methylene chloride, cooled to −70° C. by addition of dry ice to the solution, was added dropwise with moderate stirring a solution of 160.0 g (1.0 mole) of bromine in 200 ml of methylene chloride within about one hour. The reaction mixture was allowed to warm up to room temperature over a three hour period and then was kept at room temperature for one additional hour. (After addition of about 80% of the total bromine solution, the methylene chloride solution became turbid. It cleared up when the temperature of the solution rose to about −45° C. after complete addition of bromine.) The solvent was removed in vacuo in a bath kept below 50° C. The residual light yellow solid, 2,3,5,6-tetrabromo-2,6-dimethyl-4-heptanone (229.2 g, 100% of theory, melting at 74°–83° C.) was used for dehydrobromination without further purification.

Dehydrobromination of 2,3,5,6-tetrabromo-2,6-dimethyl-4-heptanone.

The above crude, 2,3,5,6-tetrabromo-2,6-dimethyl-4-heptanone was dissolved in 200 ml. of methylene chloride and the solution was cooled to about −10° C. with an ice-methanol bath. To this solution, 250 ml of pyridine was added under a nitrogen atmosphere. The mixture was stirred about fifteen hours while the temperature was maintained at less than 25° C. The reaction mixture was poured into 800 ml of 15% solution of sulfuric acid in ice water (prepared by the addition of ice to 400 ml of 30% of sulfuric acid solution until the total volume reached 800 ml). The aqueous layer was extracted with three 150 ml portions of methylene chloride. The combined methylene chloride extracts were washed with two 250 ml portions of 30% aqueous sulfuric acid and then with three 300 ml portions of water, dried over anhydrous sodium sulfate and evaporated under reduced pressure (pot temperature less than 50° C.). 3,5-Dibromo-2,6-dimethyl-2,5-heptadiene-4-one (wt. 157.75 g) was obtained as a light brown oil containing about 8% solvent.

EXAMPLE 2

2,3,5,6-Tetrabromo-2,6-dimethyl-4-heptanone was prepared as in Example 1 except that the solvent was not completely removed in vacuo. Instead the solvent was removed in vacuo until the volume of the reaction mixture was reduced to 200 ml. To this solution, cooled to about −10° C., 250 ml of pyridine was added under nitrogen atmosphere. The mixture was left stirring for about 15 hr. while the temperature was kept below 25° C. The reaction mixture was poured into 800 ml of 15% solution of sulfuric acid in ice water. The aqueous layer was extracted with three 150 ml portions of methylene chloride. The combined methylene chloride extracts were washed with two 250 ml portions of 30% aqueous sulfuric acid and then with three 300 ml portions of water, dried over anhydrous sodium sulfate and evaporated under reduced pressure (pot temperature less than 50° C.). 3,5-Dibromo-2,6-dimethyl-2,5-heptadiene-4-one, 158 g, was obtained as a light brown oil, containing less than 10% solvent.

Cyclization of 3,5-Dibromo-2,6-dimethyl-2,5-heptadiene-4-one to 3-bromo-2-hydroxy-4,4,5,5-tetramethylcyclopenta-2-enone.

To 203 ml of 85% aqueous sulfuric acid, which was cooled in an ice-methanol bath to −5° C., was added 79.0 g of the crude 3,5-dibromo-2,6-dimethyl-2,5-heptadiene-4-one, at such a rate as to keep the temperature below 20° C. There was an evolution of bromine and of hydrogen bromide. In order to remove the gaseous material from the sulfuric acid solution, a stream of nitrogen gas was bubbled through the solution from the bottom of the reaction vessel. After stirring in a water bath (28° C.) overnight (15 hr), the green sulfuric acid solution was added dropwise over a period of about 1 hr. to a liter of ice-water which contained 26 g of sodium sulfite. The aqueous suspension was stirred at room temperature for 3 hr and was extracted with three 150 ml portions of methylene chloride. The combined methylene chloride extracts were washed with two 300 ml portions of water, dried over anhydrous sodium sulfate and methylene chloride was removed under a reduced pressure. The solid residue was dissolved in 400 ml of boiling hexane. The solution was treated with charcoal and evaporated to a total volume of 200 ml, left at room temperature overnight and filtered. The product was washed with three 20 ml portions of cold hexane to give 41.80 g of light yellow needles, m.p. 115.5° to 116.5° C. (a 67% yield).

EXAMPLE 3

Large scale preparation of tetrabromophorone using conventional bromination and recrystallization.

To a solution of 16.56 kg of phorone (120 moles) in 8 liters carbon tetrachloride cooled with ice-water to 5°–10° C. was added, dropwise, 38.4 kg of bromine dissolved in 6.5 liters carbon tetrachloride, with stirring, and at such a rate as to keep temperature at 10°–15° C. The reaction mixture was allowed to stand for 2 hrs. and then the solvent was removed in vacuo leaving an oily residue. This residue was crystallized from 46 liters of methanol to give 29.95 kg (55%) of a colorless crystalline solid.

EXAMPLE 4

Large scale preparation of bromoreductic acid using method of this invention.

To a solution of 17.1 kg of phorone (124 moles) in 26.1 gallons of methylene chloride, cooled to −70° C. by addition of liquid carbon dioxide to the solution, was added with moderate stirring a solution of 39.6 kg of bromine in 6.6 gallons of methylene chloride within about two hours. The reaction mixture was allowed to warm up to room temperature over a two hour period and then was kept at room temperature for one additional hour. Solvent was removed by vacuum distillation (kept below 50° C.) to a volume of 72 liters.

To this solution, cooled to about −10° C., 61 kg of pyridine was added under a nitrogen atmosphere. The mixture was stirred for fifteen hours while the temperature was kept below 25° C. The reaction mixture was added into 36 gallons of a 15% solution of sulfuric acid in ice water. The aqueous layer was extracted with three 37 liter portions of methylene chloride. The combined methylene chloride extracts were washed with two 18 gallon portions of 30% sulfuric acid and then with two 22 gallon portions of water and distilled under reduced pressure (temperature less than 50° C.) to a total volume of 27 liters.

To 111.4 liters of 85% aqueous sulfuric acid which was cooled to −5° C., was added, the 27 liters of the crude dibromophorone, at such a rate as to keep the temperature below 25°. There was a evolution of hydrogen bromide. In order to remove the gaseous material from the sulfuric acid solution, a stream of nitrogen gas was bubbled through the solution from the bottom of the reactor. After stirring at about 28° C. overnight, the green sulfuric acid solution was added, over a period of 1 hour, to 156 gallons of ice water which contained 1.6 kg of sodium sulfite. The aqueous suspension was stirred at room temperature for half an hour and was extracted with two 10 gallon portions of methylene chloride. The combined methylene chloride extracts were washed with two 25 gallon portions of water and methylene chloride was removed under a reduced pressure to a total volume of 54 liters. The residue was dissolved in 35 gallons of hexane and 17.5 gallons of hexane was distilled off the solution. An additional 17.5 gallons of fresh hexane was added and the solution was treated with 300 g of charcoal. 500 g of a filtering aid was added. The solution was evaporated to a total volume of 17.5 gallons. The hexane solution was left at room temperature overnight, filtered and the product was washed with two 2 gallon portions of cold hexane to give 18.8 kg (65% overall yield) of light yellow needles of bromoreductic acid m.p. 114°–116°.

EXAMPLE 5

Attempted preparation of bromoreductic acid without purification of intermediates using conventional bromination.

To 20 g of phorone in 100 ml chloroform was added dropwise 47.3 g of bromine in 16 ml chloroform with stirring and at such a rate to keep the temperature at 7°–8° C. The reaction mixture was allowed to stand for 2 hrs. and then the solvent was removed in vacuo leaving an oily residue which solidified upon standing. To 66 ml of pyridine cooled with ice water was added the residual solid with stirring and portionwise at such a rate to keep the temperature below 8° C. After 15 minutes, a solid started precipitating out from the solution. The reaction mixture was allowed to come to room temperature and poured into 225 ml of water. The water solution was extracted twice with 30 ml each of methylene chloride.

To 144 ml of concentrated sulfuric acid cooled to 5° C. was added the methylene chloride solution of dibromophorone prepared above, with stirring, at such a rate as to keep the temperature of the reaction mixture between 5°–20° C. The reaction mixture was stirred at room temperature overnight (18 hr) under a stream of nitrogen. The mixture was then poured into 800 ml of ice. The solid was filtered and washed with water. The crude product was dissolved in 120 ml of ethanol and poured with stirring into 500 ml of cold water. After cooling, the precipitate was filtered and washed with water and dried at 40° C. in a vacuum oven to give 19 g (30%) (wet) of bromoreductic acid. A sample left overnight in a vacuum oven to dry decomposed.

Since certain changes may be made in the above method without departing from the scope of the invention herein involved, it is intended that all matter contained in the above description shall be interpreted as illustrative and not in a limiting sense.

What is claimed is:

1. A process for the preparation of 3-bromo-2-hydroxy-4,4,5,5-tetramethyl cyclopenta-2-enone which comprises the sequential steps of:
   (a) reacting bromine with at least about twenty-five moles of 2,6-dimethyl-2,5-heptadiene-4-one in a molecular equivalent ratio of about two to one in a suitable solvent at a temperature below about −20° C. whereby 2,3,5,6-tetrabromo-2,6-dimethyl-4-heptanone is formed in solution,
   (b) adding to said solution a dehydrobromination agent in an amount sufficient to dehydrobrominate said 2,3,5,6-tetrabromo-2,6-dimethyl-4-heptanone to 3,5-dibromo-2,6-dimethyl-2,5-heptadiene-4-one, and
   (c) adding said 3,5-dibromo-2,6-dimethyl-2,5-heptadiene-4-one to an amount of a very strong protic acid equivalent to the amount of said 2,6-dimethyl-2,5-heptadiene-4-one reacted with said bromine, at such a rate as to keep the temperature of the reaction mixture below 20° C.

2. The process of claim 1 wherein said solvent is selected from the group consisting of carbon tetrachloride, chloroform and methylene chloride.

3. The process of claim 2 wherein said dehydrobromination agent is selected from the group consisting of 1,4-diazabicyclo[2,2,2]octane, morpholine, piperidine and pyridine.

4. The process of claim 1 wherein said very strong protic acid is selected from the group consisting of trifluoroacetic acid, polyphosphoric acid and concentrated sulfuric acid.

5. A process for preparing 3-bromo-2-hydroxy-4,4,5,5-tetramethylcyclopenta-2-enone which comprises the sequential steps of:
   (a) reacting bromine with at least twenty-five moles of 2,6-dimethyl-2,5-heptadiene-4-one in an equivalent ratio of about 2:1 in a solvent selected from the group consisting of carbon tetrachloride, chloroform and methylene chloride at a temperature below −20° C. to provide 2,3,5,6-tetrabromo-2,6-dimethyl-4-heptanone in solution;
   (b) adding a dehydrobromination agent selected from the group consisting of 1,4-diazabicyclo [2,2,2]octane, morpholine, piperidine and pyridine in an amount sufficient to dehydrobrominate said 2,3,5,6-tetrabromo-2,6-dimethyl-4-heptanone to 3,5-dibromo-2,6-dimethyl-2,5-heptadiene-4-one, and
   (c) adding said 3,5-dibromo-2,6-dimethyl-2,5-heptadiene-4-one to an amount of a very strong protic acid selected from the group consisting of trifluoracetic acid, polyphosphoric acid and concentrated sulfuric acid equivalent to the amount of said 2,6-dimethyl-2,5-heptadiene-4-one reacted with said bromine, at such a rate as to keep the temperature of the reaction mixture below 20° C.

6. The process of claim 5 wherein said solvent is methylene chloride.

7. The process of claim 6 wherein said temperature in step (a) is −70° C.

8. The process of claim 5 wherein said dehydrobromination agent is pyridine.

9. A process which comprises the steps of:
   (a) reacting bromine with about one hundred twenty-five moles of 2,6-dimethyl-2,5-heptadiene-4-one in an equivalent ratio of 2:1 in methylene chloride at −70° C. to provide 2,3,5,6-tetrabromo-2,6-dimethyl-4-heptanone in solution:
   (b) adding a quantity of pyridine at least equal in volume to said solution, to form 3,5-dibromo-2,6-dimethyl-2,5-heptadiene-4-one; and
   (c) adding said 3,5-dibromo-2,6-dimethyl-2,5-heptadiene-4-one to about one hundred seventy-five moles of concentrated sulfuric acid at such a rate as to keep the temperature of the reaction mixture below 20° C.

* * * * *